United States Patent
Rethy et al.

(10) Patent No.: US 9,427,251 B2
(45) Date of Patent: Aug. 30, 2016

(54) SABER TOOTH HARVESTER

(71) Applicant: Covidien LP, Mansfield, MA (US)

(72) Inventors: Csaba L. Rethy, Westport, CT (US); Gregg C. Krehel, Newtown, CT (US)

(73) Assignee: Covidien LP, Mansfield, MA (US)

( * ) Notice: Subject to any disclaimer, the term of this patent is extended or adjusted under 35 U.S.C. 154(b) by 227 days.

(21) Appl. No.: 14/197,382

(22) Filed: Mar. 5, 2014

(65) Prior Publication Data

US 2014/0277049 A1 Sep. 18, 2014

Related U.S. Application Data

(60) Provisional application No. 61/779,198, filed on Mar. 13, 2013.

(51) Int. Cl.
*A61B 17/00* (2006.01)
*A61B 17/3205* (2006.01)
(Continued)

(52) U.S. Cl.
CPC ....... *A61B 17/3205* (2013.01); *A61B 18/1445* (2013.01); *A61B 2018/00083* (2013.01);
(Continued)

(58) Field of Classification Search
CPC ................. A61B 2017/2918; A61B 2017/0688–2017/07285; A61B 17/32015; A61B 17/3207; A61B 17/068–17/07207; A61B 2017/0016; A61B 2017/00589; A61B 2017/00607; A61B 2017/00976; A61B 2017/126; A61B 2017/1412; A61B 2017/1415; A61B 2017/1452; A61B 2017/1457; A61B 10/02–10/06; A61B 2018/00595; A61B 2018/00601; A61B 2018/0016; A61B 2018/00589; A61B 2018/00607; A61B 2018/00976; A61B 2018/1405–2018/1495; A61B 2018/126; A61B 18/14–18/1492; A61B 17/295; A61B 17/28; A61B 17/29; A61B 17/3201; A61B 17/285; A61B 17/0467; A61B 17/32; A61B 17/12009; A61B 17/128; A61B 17/1285; A61B 2017/320016; A61B 2017/0488
USPC .......... 606/205–208, 37, 39, 40, 51, 52, 49, 606/45, 46, 48, 50, 32, 47, 167, 174, 139, 606/142, 143; 600/562–567
See application file for complete search history.

(56) References Cited

U.S. PATENT DOCUMENTS 5,643,294 A * 7/1997 Tovey ............... A61B 17/29
606/148
5,683,388 A 11/1997 Slater
(Continued)

OTHER PUBLICATIONS

Partial European Search Report from EP 14 15 9050 dated Jun. 24, 2014.
(Continued)

*Primary Examiner* — Melanie Tyson
*Assistant Examiner* — Majid Jamialahmadi

(57) ABSTRACT

A surgical instrument includes a handle assembly, an elongate body, a tool assembly, and an electrical energy source. The handle assembly includes an actuation knob. The elongate body extends distally from the handle assembly and defines a longitudinal axis. In particular, tool assembly is operatively coupled to the handle assembly and extends from a distal end of the elongate body. The tool assembly includes first and second jaw members each including an electrically conductive cutting element. The cutting elements are operatively coupled to the actuation knob. In particular, the cutting elements are movable between a first position in which the cutting elements are disposed within the respective jaw members and a second position in which the cutting elements extend out of the respective jaw members and are in general vertical registration with each other such that electrical energy can be transferred from the first jaw member to the second jaw member.

19 Claims, 7 Drawing Sheets

(51) Int. Cl.
*A61B 18/14* (2006.01)
*A61B 18/00* (2006.01)

(52) U.S. Cl.
CPC ............... *A61B2018/00595* (2013.01); *A61B 2018/00601* (2013.01); *A61B 2018/00642* (2013.01); *A61B 2018/00702* (2013.01); *A61B 2018/00875* (2013.01); *A61B 2018/1457* (2013.01); *A61B 2018/1475* (2013.01)

(56) References Cited

U.S. PATENT DOCUMENTS

| | | | |
|---|---|---|---|
| 5,746,216 A | 5/1998 | Turturro et al. | |
| 5,893,873 A * | 4/1999 | Rader | A61B 17/2909 606/205 |
| 5,908,420 A * | 6/1999 | Parins | A61B 18/1445 606/170 |
| 6,099,483 A | 8/2000 | Palmer et al. | |
| 6,193,671 B1 | 2/2001 | Turturro et al. | |
| 6,632,182 B1 | 10/2003 | Treat | |
| 8,336,754 B2 | 12/2012 | Cappola et al. | |
| 2002/0013583 A1 | 1/2002 | Camran et al. | |
| 2004/0162551 A1 | 8/2004 | Brown et al. | |
| 2005/0113826 A1* | 5/2005 | Johnson | A61B 18/1442 606/45 |
| 2007/0073185 A1* | 3/2007 | Nakao | A61B 10/06 600/564 |
| 2007/0173814 A1* | 7/2007 | Hixson | A61B 18/1445 606/51 |
| 2008/0086154 A1 | 4/2008 | Taylor et al. | |
| 2010/0022837 A1 | 1/2010 | Ishiguro et al. | |
| 2011/0040308 A1* | 2/2011 | Cabrera | A61B 17/0469 606/144 |
| 2011/0238057 A1 | 9/2011 | Moss et al. | |
| 2012/0245427 A1 | 9/2012 | Kleyman | |
| 2012/0283520 A1 | 11/2012 | Kleyman | |
| 2013/0012983 A1 | 1/2013 | Kleyman | |
| 2014/0074084 A1* | 3/2014 | Engeberg | A61B 18/1206 606/33 |

OTHER PUBLICATIONS

European Search Report from EP 14 15 9050 dated Oct. 9, 2014.

* cited by examiner

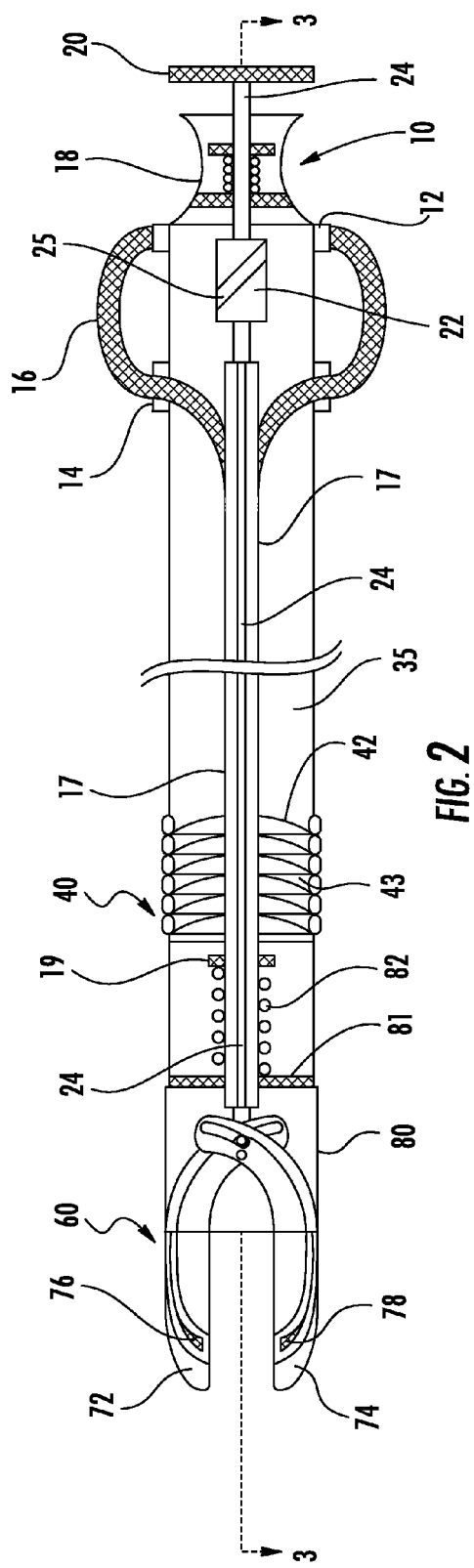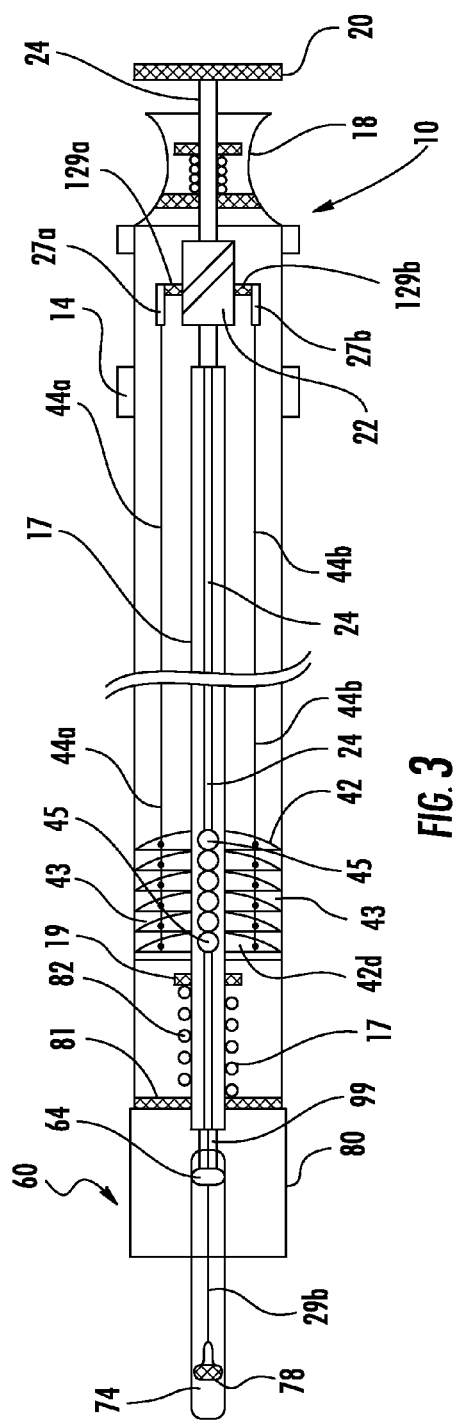

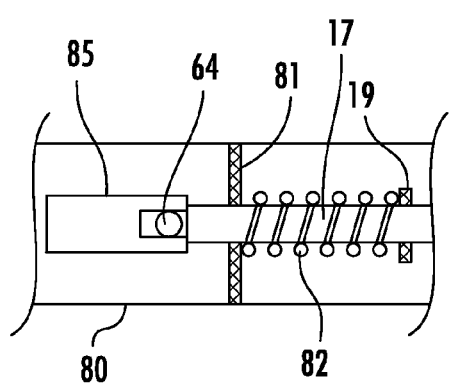
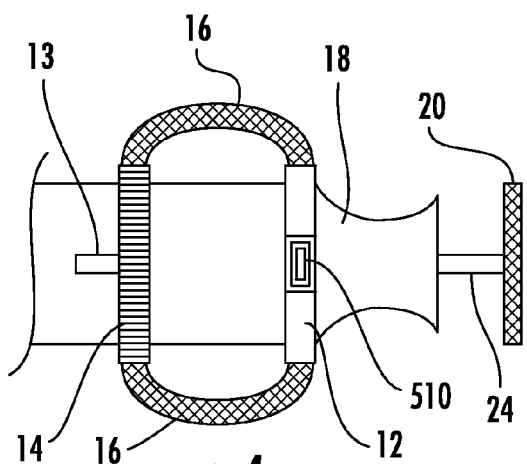
FIG. 5    FIG. 4
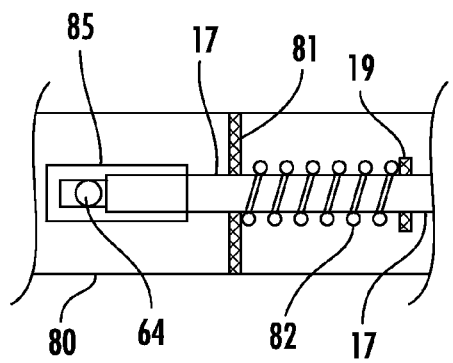
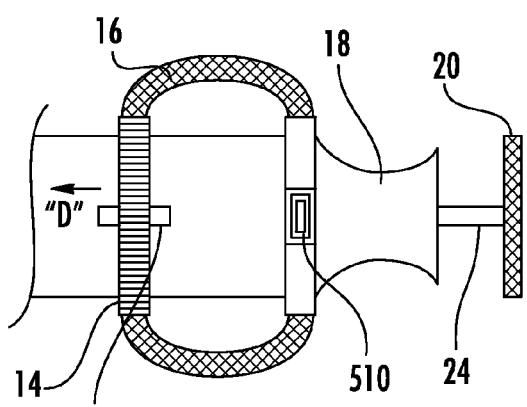
FIG. 7    FIG. 6

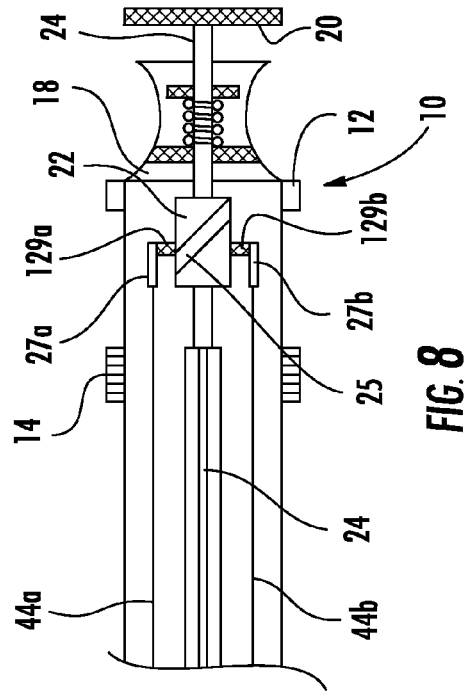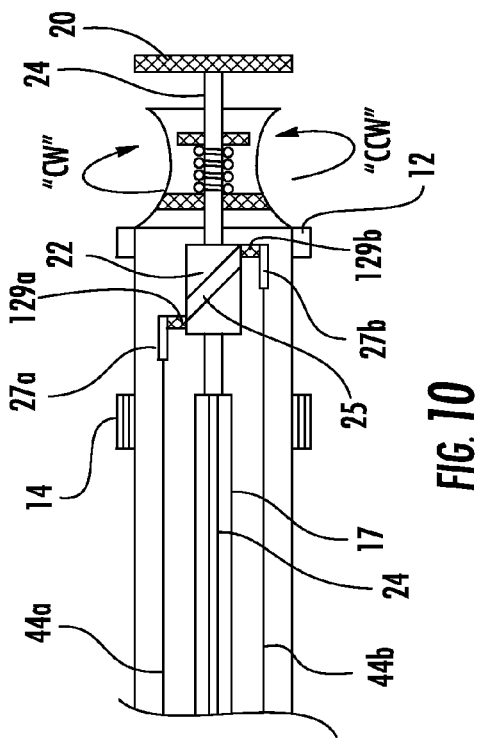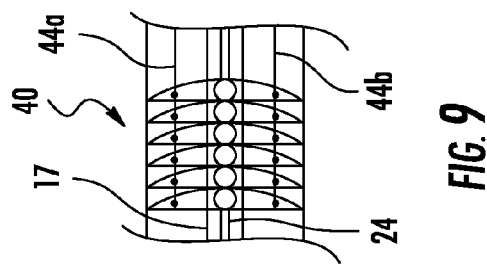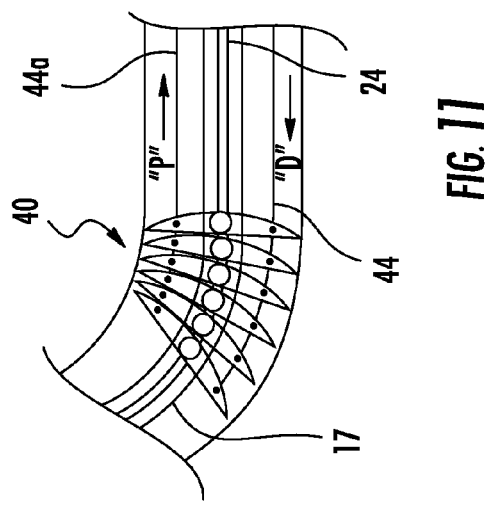

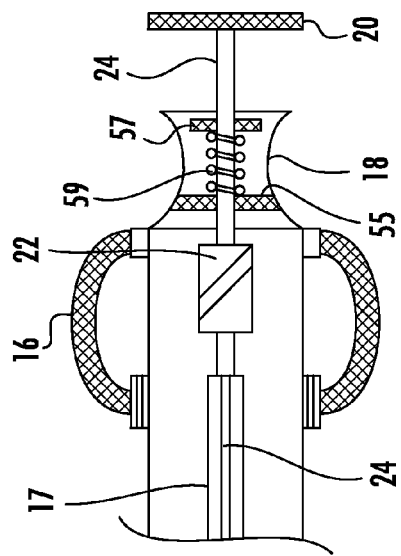
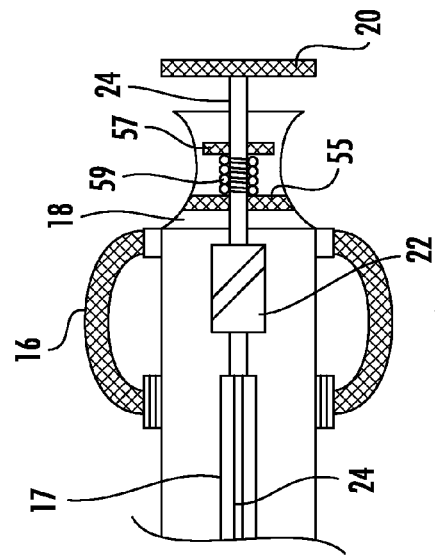
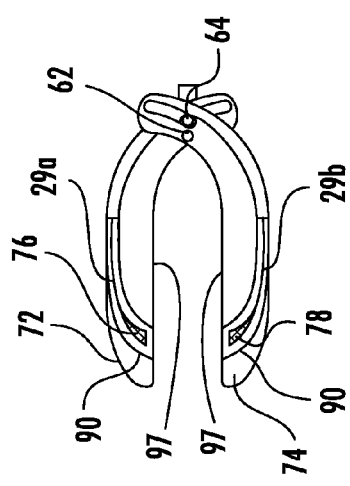
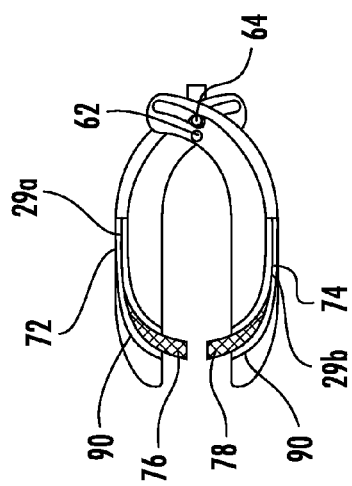

SABER TOOTH HARVESTER

CROSS-REFERENCE TO RELATED APPLICATIONS

This application claims the benefit of and priority to U.S. Provisional Patent Application No. 61/779,198, filed Mar. 13, 2013, the entire disclosure of which is incorporated by reference herein.

BACKGROUND

1. Technical Field

The present disclosure relates to a surgical instrument, and more particularly, to a tissue harvesting device that is introduced into a thoracic cavity to remove specimens from underlying body structures.

2. Background of Related Art

The development of endoscopic video capability and instrumentation has resulted in the application of diagnostic and therapeutic thoracoscopy, also known as video-assisted thoracic surgery (VATS), to many disease processes encountered in thoracic medicine. VATS is a technique in which small diameter instruments such as cameras, graspers, forceps, retractors, dissectors, clamps, and so forth are inserted through small openings in the body to perform surgical procedures within the thoracic cavity. By utilizing a VATS procedure for exploring, diagnosing, and treating disease processes within the thoracic cavity, the pain, morbidity, and long recovery duration of more invasive procedures can often be avoided.

Therefore, there is a need in the art for an improved system and method for the capturing of body tissue samples. More particularly, there is a need for a system and method for capturing thoracic lymph nodes suspected of being cancerous.

SUMMARY

In accordance with an embodiment of the present disclosure, there is provided a surgical instrument including a handle assembly, an elongate body extending distally from the handle assembly and defining a longitudinal axis, a tool assembly operatively coupled to the elongate body, and an electrical energy source. The handle assembly includes an actuation knob. The tool assembly extends from a distal end of the elongate body. The tool assembly includes first and second jaw members each including an electrically conductive cutting element. The cutting elements are operatively coupled to the actuation knob. In particular, the cutting elements are movable between a first position in which the cutting elements are disposed within the respective jaw members and a second position in which the cutting elements extend out of the respective jaw members and are in general vertical registration with each other such that electrical energy can be transferred from the first jaw member to the second jaw member. The electrical energy source provides electrical energy to the cutting elements.

In an embodiment, the first and second jaw members may be movable between a spaced apart position and an approximated position in which the jaw members are adjacent to each other to clamp tissue therebetween. Moreover, the first and second jaw members may each define a channel configured to slidably receive the respective cutting element.

In another embodiment, the surgical instrument may further include an actuation rod interconnecting the actuation knob and the cutting elements, wherein translation of the actuation knob causes transition of the cutting elements between the first and second positions, and rotation of the actuation knob causes rotation of the jaw members about the longitudinal axis.

In yet another embodiment, the surgical instrument may further include an approximation rod extending through the elongate body and operatively coupled to the first and second jaw members. In particular, translation of approximation rod may move the first and second jaw members between the spaced apart and approximated positions. The approximation rod and the actuation rod may be concentrically arranged. Furthermore, the handle assembly may include a slidable collar configured and adapted to slide over the elongate body. The slidable collar may be operatively coupled with the approximation rod for a concomitant translation therewith.

In still yet another embodiment, the surgical instrument may further include an articulation assembly including a plurality of articulation links pivotably coupled to each other and a pair of articulation cables interconnecting the plurality of articulation links. The pair of articulation cables may be operatively coupled to the handle assembly.

The handle assembly may further include a rotatable hub defining a helical groove on an outer wall thereof, wherein proximal ends of the pair of articulation cables are configured and adapted to slidably engage the helical groove, whereby rotation of the rotatable hub translates the pair of articulation cables in opposite directions. The tool assembly may be rotatable about the longitudinal axis.

In an embodiment, the cutting elements may be substantially dull and only capable of cutting tissue by providing electrical energy to the cutting elements. Alternatively, the cutting elements may include blade portions that are capable of cutting tissue without the electrical energy. In another embodiment, the first and second jaw members may each include a tissue contacting surface having teeth configured and adapted to grasp tissue.

In accordance with another aspect of the present disclosure, there is provided a method of removing tissue. The method includes providing a surgical instrument including an elongate body and a tool assembly secured to a distal end of the elongate body. In particular, the tool assembly includes first and second jaw members each including an electrically conductive cutting element slidably disposed therein. The cutting elements are movable between a first position in which the cutting elements are disposed within the respective jaw members and a second position in which the cutting elements are disposed in general vertical registration to each other such that electrical energy can be transferred through tissue positioned between the cutting elements to cut tissue. The method further includes introducing the surgical instrument into a patient, advancing the tool assembly toward a target tissue within the patient, placing tissue between the first and second jaw members, positioning the cutting elements in general vertical registration to each other, cutting tissue positioned between the cutting elements, and extracting tissue from the target surgical site.

In an embodiment, cutting tissue positioned between the cutting elements may include supplying electrical energy to the cutting elements.

In another embodiment, the surgical instrument may further include an articulation mechanism for articulating the tool assembly. In addition, the surgical instrument may further include an actuation knob operatively coupled to the cutting elements, wherein translation of the actuation knob causes transition of the cutting elements between the first and second positions, and rotation of the actuation knob causes rotation of the first and second jaw members about the longitudinal axis.

In still yet another embodiment, the method may further include rotating the tool assembly about the longitudinal axis.

BRIEF DESCRIPTION OF THE DRAWINGS

Various embodiments of the present disclosure are described hereinbelow with reference to the drawings, wherein:

FIG. 2 is a longitudinal cross-sectional view of the surgical instrument of FIG. 1;

FIG. 3 is a cross-sectional view taken along section line 3-3 in FIG. 2;

FIG. 4 is a partial cross-sectional view of a handle assembly of the surgical instrument of FIG. 1;

FIG. 5 is a partial cross-sectional view of an end effector of the surgical instrument of FIG. 1;

FIG. 6 is a partial cross-sectional view of the handle assembly of FIG. 4 illustrating actuation of an approximation handle;

FIG. 7 is a partial cross-sectional view of the end effector of FIG. 5 when the approximation handle is actuated;

FIG. 8 is a partial cross-sectional view of the handle assembly of the surgical instrument of FIG. 1;

FIG. 9 is a partial cross-sectional view of an articulation neck assembly of the surgical instrument of FIG. 1;

FIG. 10 is a partial cross-sectional view of the handle assembly of FIG. 8 illustrating rotation of an articulation knob of the handle assembly;

FIG. 11 is a partial cross-sectional view of the neck assembly of FIG. 9 when the articulation knob is rotated;

FIG. 12 is a partial cross-sectional view of the handle assembly of the surgical instrument of FIG. 1 illustrating an actuation knob in a neutral position;

FIG. 13 is a partial cross-sectional view of the handle assembly of FIG. 12 illustrating actuation of the actuation knob;

FIG. 14 is a partial cross-sectional view of a tool assembly of the end effector of the surgical instrument of FIG. 1 when the actuation knob is in the neutral position;

FIG. 15 is a partial cross-sectional view of the tool assembly of FIG. 14 when the actuation knob is actuated;

DETAILED DESCRIPTION

Figure 1:
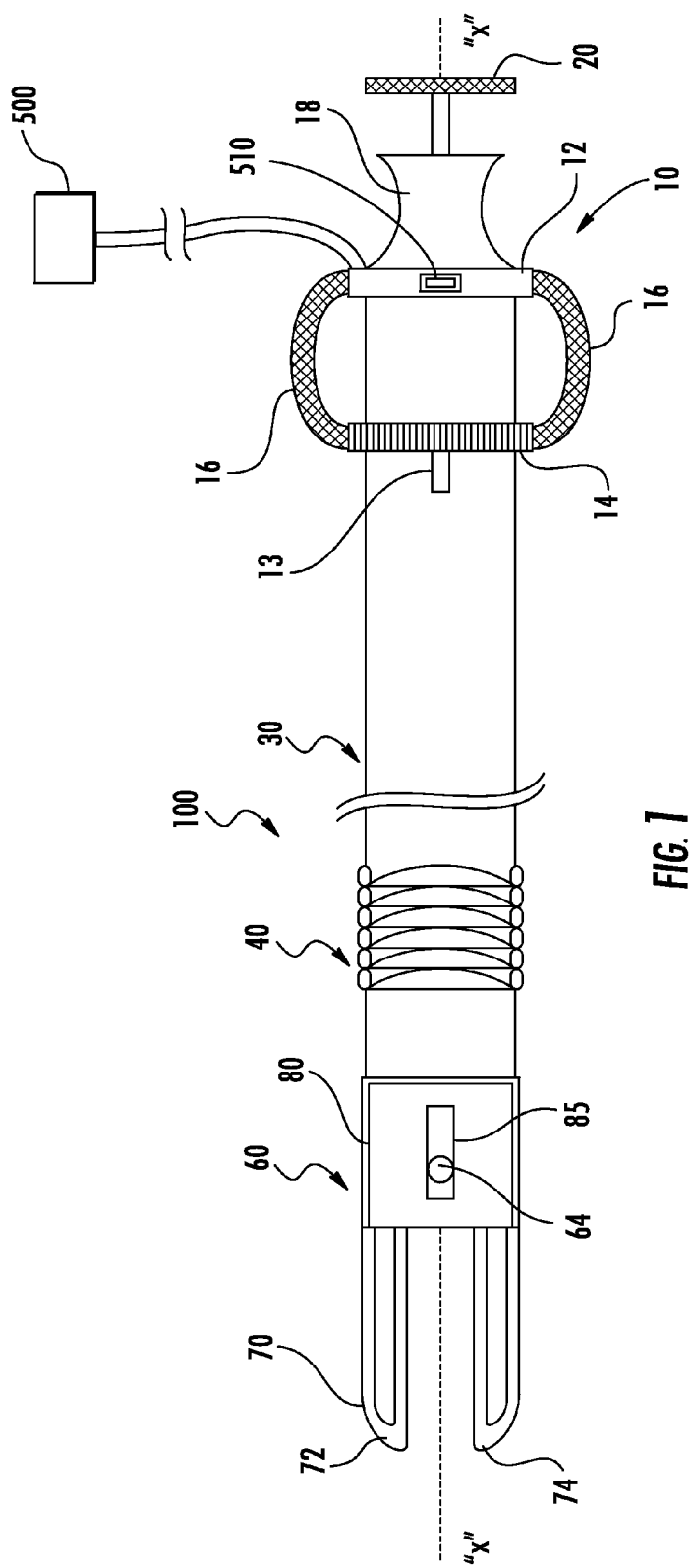
FIG. 1 is a side view of a surgical instrument in accordance with an embodiment of the present disclosure.

Embodiments of the present disclosure will now be described in detail with reference to the drawings, in which like reference numerals designate identical or corresponding elements in each of the several views. As used herein, the term "distal," as is conventional, will refer to that portion of the instrument, apparatus, device or component thereof which is farther from the user while, the term "proximal," will refer to that portion of the instrument, apparatus, device or component thereof which is closer to the user. In the following description, well-known functions or constructions are not described in detail to avoid obscuring the present disclosure in unnecessary detail. Although the present disclosure is discussed in terms of a minimally invasive thoracic procedure, the presently disclosed instrument is usable in other minimally invasive procedures.

With reference to FIG. 1, there is illustrated a surgical instrument 100 for dissecting and removing specimens, e.g., lymph nodes, during Video Assisted Thoracic Surgery (VATS) in accordance with an embodiment of the present disclosure. Lymph nodes are retrieved for specimen pathological analysis for, for example, cancer treatments.

With continued reference to FIG. 1, surgical instrument 100 includes a handle assembly 10, an elongate body 30 extending distally from handle assembly 10, an articulation neck assembly 40 secured to a distal portion of elongate body 30 and an end effector 60 operatively coupled to handle assembly 10 and extending distally from articulation neck assembly 40. End effector 60 includes a pair of jaw members 72, 74 movable from an open position for positioning tissue between jaw members 72, 74 to an approximated, clamping position for grasping tissue between jaw members 72, 74 and a pair of retractable cutting elements 76, 78 (FIG. 2) translatably disposed in respective jaw members 72, 74. Each of cutting elements 76, 78 may include an electrode configured and adapted to cauterize and cut tissue, as will be described in detail hereinbelow.

With reference now to FIGS. 2 and 3, handle assembly 10 includes an approximation handle 16, an articulation knob 18 and/or an actuation knob 20. Approximation handle 16 may be squeezed to approximate the pair of jaw members 72, 74 that are normally disposed at a first position, for example, where the jaw members are spaced apart in relation relative to one another, to a second position, for example where the jaw members are positioned substantially adjacent to one another. Upon release of approximation handle 16, the pair of approximated jaw members 72, 74 returns back to the spaced apart position. Articulation knob 18 may be rotated to provide articulation of articulation neck assembly 40 to enable, for example, a side-to-side, movement of end effector 60. Actuation knob 20 may be moved distally to slide cutting elements 76, 78 out of jaw members 72, 74 and in general vertical registration with each other to cauterize or cut tissue specimen during VATS. Additionally, actuation knob 20 may be rotated to selectively position end effector 60 to any rotational orientation about a longitudinal axis "X-X" (FIG. 1) of the surgical instrument 100.

In particular, approximation handle 16 is secured to a base member 12 of handle assembly 10. In addition, making reference to FIGS. 2 and 3, approximation handle 16 is coupled to an approximation rod 17 translatably disposed within elongate body 30. Approximation rod 17 is operatively coupled with jaw members 72, 74, as will be described in detail hereinbelow. Approximation handle 16 extends through a slidable collar 14 and is coupled with approximation rod 17. Slidable collar 14 includes at least a pair of protrusions or camming pins (not shown) extending radially inward that engages a pair of respective opposing apertures or slots 13 (FIG. 1) defined in elongate body 30. In this manner, when approximation handle 16 is squeezed, the camming pins engage and slide within respective slots 13, and slidable collar 14 slides on an outer wall of elongate body 30 along slots 13. In this manner, translation of slidable collar 14 causes translation of approximation rod 17. Such an arrangement facilitates secure translation of approximation rod 17 within a working channel 35 defined in elongate body 30.

With particular reference to FIG. 3, approximation rod 17 extends through elongate body 30 and at least partially into end effector 60. In particular, a distal end of approximation rod 17 extends into a support member 80 of end effector 60. Support member 80 includes an anchor wall 81 extending radially inward and defining a bore configured and dimensioned to receive a distal end of approximation rod 17 therethrough. Approximation rod 17 may further include a stopper 19. Stopper 19 is fixedly attached to approximation rod 17 and translates with approximation rod 17. In particular, stopper 19 is configured and adapted to secure a biasing member 82 thereto. Under such configuration, biasing member 82 is positioned between stopper 19 and anchor wall 81 of support member 80. The bore defined in anchor wall 81 is dimensioned to only receive approximation rod 17 therethrough. In this manner, when approximation handle 16 is squeezed (FIGS. 4 and 6) inwardly toward elongate body 30, approximation rod 17 is translated distally (FIGS. 5 and 7), and thereby compressing biasing member 82 (FIG. 7) substantially between stopper 19 and anchor wall 81. Translating approximation rod 17 distally approximates jaw members 72, 74 to a closed position, as will be discussed in detail hereinbelow. Under such configuration, jaw members 72, 74 are biased toward spaced apart position, whereby release of approximation handle 16 urges jaw members 72, 74 to the spaced apart position. It is also contemplated that a locking mechanism (not shown) may be added to handle assembly 10 to lock jaw members 72, 74 in a desired position. Reference may be made to U.S. Pat. No. 8,336,754, filed on Feb. 4, 2011, and U.S. Patent Application Publication No. 2013/0012983, filed on Jul. 9, 2012, the entire contents of each of which are incorporated herein by reference, for a detailed discussion of the construction and operation of a locking mechanism.

With reference back to FIGS. 2 and 3, handle assembly 10 further includes articulation knob 18 to enable, for example, side-to-side, movement of end effector 60 at articulation neck assembly 40. Other types of movement of end effector 60, such as up-and-down or rotational, are also envisioned. Articulation knob 18 is rotatably secured to base member 12. In particular, articulation knob 18 is rotatably coupled with a rotatable hub 22 rotatably disposed within elongate body 30 for concomitant rotation therewith. Rotatable hub 22 defines a helical groove 25 on an outer surface of thereof. Rotatable hub 22 further includes a pair of arms 27a, 27b (FIG. 3) each having a respective finger 129a, 129b. Each finger 129a, 129b is configured and adapted to slidably engage helical groove 25 of rotatable hub 22. A distal end of each arm 27a, 27b is coupled with respective articulation cable 44a, 44b (FIG. 3). When articulation neck assembly 40 is in a neutral position, as shown in FIGS. 3 and 9, articulation neck assembly 40 is aligned with a longitudinal axis "X-X" (FIG. 1) of surgical instrument 100, and fingers 129a, 129b are aligned at a longitudinal position. However, upon rotation of articulation knob 18 about longitudinal axis "X-X," in either direction "CW," "CCW" (FIG. 10), fingers 129a, 129b travel in opposite longitudinal directions along helical groove 25 of rotatable hub 22. In this manner, one of arms 27a, 27b pulls the respective articulation cable 44a, 44b proximally and the other arm 27a, 27b is pulled distally by the other articulation cable 44a, 44b. The simultaneous translation of articulation cables 44a, 44b in opposite directions (FIG. 11) enables articulation of neck assembly 40, which in turn provides side-to-side movement of end effector 60, as will be described in detail hereinbelow.

With continued reference to FIG. 3, handle assembly 10 includes actuation knob 20 operatively connected to an actuation rod 24. Actuation rod 24 extends through the entire length of elongate body 30 and is operatively coupled with cutting elements 76, 78 retractably disposed within respective jaw member 72, 74. Actuation rod 24 is configured and dimensioned to extend through articulation knob 18 and approximation rod 17, as well as rotatable hub 22. In particular, each cutting element 76, 78 is retractably disposed in channel 90 (FIG. 14) of respective jaw member 72, 74 and is operatively connected to flexible shafts 29a, 29b (FIG. 15), respectively. Flexible shafts 29a, 29b extend through a lumen defined in a connector 99 and are coupled to actuation rod 24 (FIG. 3). Flexible shaft 29a, 29b may be at least sufficiently flexible to accommodate the contour of channels 90 in respective jaw members 72, 74. Flexibility may be obtained in any number of ways. For example, flexible shaft 29a, 29b may be made of a flexible material, and/or may be comprised of a number of segments, and/or may have portions of material removed from it, for example as grooves, to increase flexibility.

With reference to FIG. 12, actuation rod 24 first extends through articulation knob 18. Articulation knob 18 may define a passageway or a lumen. In particular, the lumen includes an anchor wall 55 similar to anchor wall 81 of support member 80. Actuation rod 24 may include a stopper 57. Similar to stopper 19 of approximation rod 17, stopper 57 is fixedly attached to actuation rod 24 and translates with actuation rod 24. A biasing member 59 is securely interposed between anchor wall 55 and stopper 57. When actuation knob 20 is moved distally (FIG. 13), actuation rod 24 is translated distally and stopper 57 compresses biasing member 59 against anchor wall 55. As such, actuation rod 24 translates against the bias of biasing member 59. Actuation rod 24 extends through rotatable hub 22 and through approximation rod 17, as shown in FIG. 2. Actuation rod 24 is coupled with flexible shafts 29a, 29b, whereby translation of actuation rod 24 causes concomitant translation of flexible shafts 29a, 29b, which in turn moves cutting elements 76, 78 in and out of respective jaw members 72, 74.

With reference to FIGS. 12-15, when actuation knob 20 is in a neutral position (FIGS. 12 and 14), cutting elements 76, 78 are positioned substantially within respective jaw member 72, 74. However, when actuation knob 20 is moved distally (FIG. 13) cutting elements 76, 78 slide out of channels 90 of respective jaw members 72, 74 against the bias of biasing member 59 (FIGS. 13 and 15). Release of actuation knob 20 allows biasing member 59 to expand and urges stopper 57 proximally which moves actuation rod 24 proximally and cutting elements 76, 78 back into respective channel 90 of jaw member 72, 74. However, it is further contemplated that actuation knob 20 may include a locking mechanism (not shown) that locks the desired retraction positions of cutting elements 76, 78 in and out of respective channels 90.

With reference back to FIGS. 2 and 3, elongate body 30 defines a working channel 35 dimensioned and configured to accommodate therein rotatable hub 22, actuation rod 24, articulation cable 44a, 44b and approximation rod 17, as described hereinabove. While elongate body 30, as shown, is substantially straight, it is also contemplated that elongate body 30 may be relatively flexible to facilitate insertion into a patient's body. A distal portion of elongate body 30 is coupled with articulation neck assembly 40. Articulation neck assembly 40 includes a plurality of articulation links 42. Each articulation link 42 is pivotally associated with adjacent articulation links 42. Each articulation link 42 may have a semi-spherical shape, whereby adjacent links 42 defines a gap 43 therebetween. Such gap 43 enables pivotal rotation of each link 42. Other shapes for articulation links, such as spherical or crescent, are also contemplated. In addition, each link 42 may define a bore on each opposing side of link 42 with respect to pivot axis 45 (FIG. 3). Each bore is configured and dimensioned to receive therethrough respective articulation cable 44a, 44b. In particular, distal-most link 42d is securely connected to articulation cables 44a, 44b. In this manner, translation of articulation cables 44a, 44b in opposite directions enables articulation movement of neck assembly 40, thereby enabling, for example, a side-to-side, movement of end effector 60 (FIG. 11).

Figure 16:
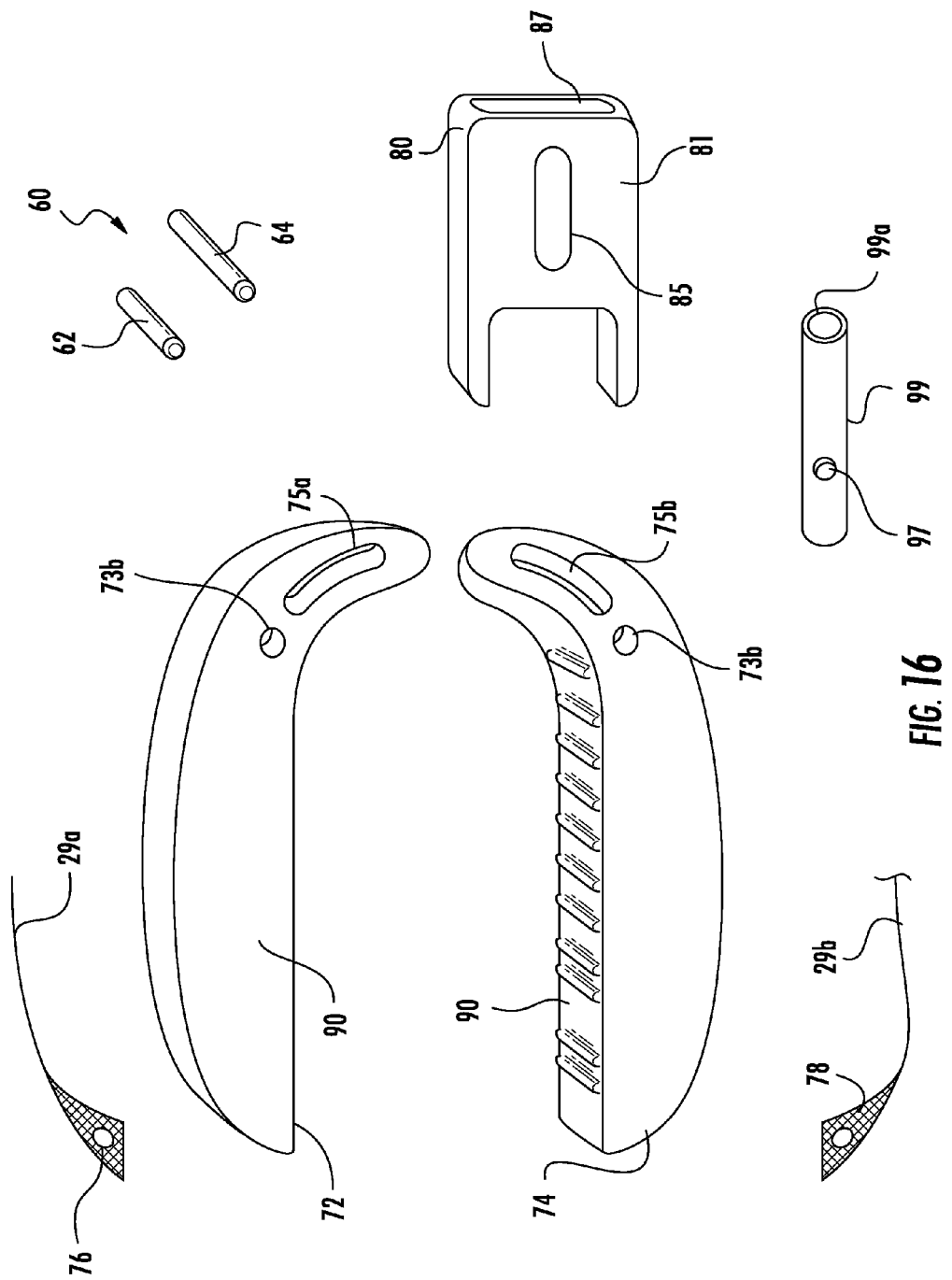
FIG. 16 is an exploded perspective view of the end effector of the surgical instrument of FIG. 1 with parts separated.

With reference now to FIGS. 1 and 16, end effector 60 is operatively coupled to handle assembly 10 and extends distally from articulation neck assembly 40. End effector 60 includes a tool assembly 70 and a support member 80. Tool assembly 70 includes a pair of jaw members 72, 74 that is movable from an open position for positioning tissue between jaw members 72, 74 to a clamping position for grasping tissue between jaw members 72, 74. In particular, each jaw member 72, 74 may define a pivot bore 73a, 73b, whereby jaw members 72, 74 are pivotally connected to each other by a pivot pin 62 in pivot bore 73a, 73b. In addition, each jaw member 72, 74 may define a camming slot 75a, 75b. Each camming slot 75a, 75b defines an acute angle with respect to longitudinal axis "X-X."

Support member 80 secures end effector 60 to articulation neck assembly 40. Support member 80 may define a lumen therethrough 87 and a longitudinal slot 85 on an outer wall 81 thereof. Longitudinal slot 85 is in communication with lumen 87. A distal end of approximation rod 17 is connected to a proximal end 99a of a connector 99. Connector 99 defines a transverse bore 97 configured and dimensioned to receive camming pin 64 therein. Camming pin 64 is configured and dimensioned to slidably engage camming slots 75a, 75b of jaw members 72, 74 and longitudinal slot 85 of support member 80. Under such configuration, as camming pin 64 slidably translates along longitudinal slot 85 through translation of approximation rod 17 and connector 99, camming pin 64 slidably engages camming slots 75a, 75b defined in respective jaw members 72, 74. In this manner, translation of connector 99 through translation of approximation rod 17 enables opening and closing of jaw members 72, 74.

Figure 17:
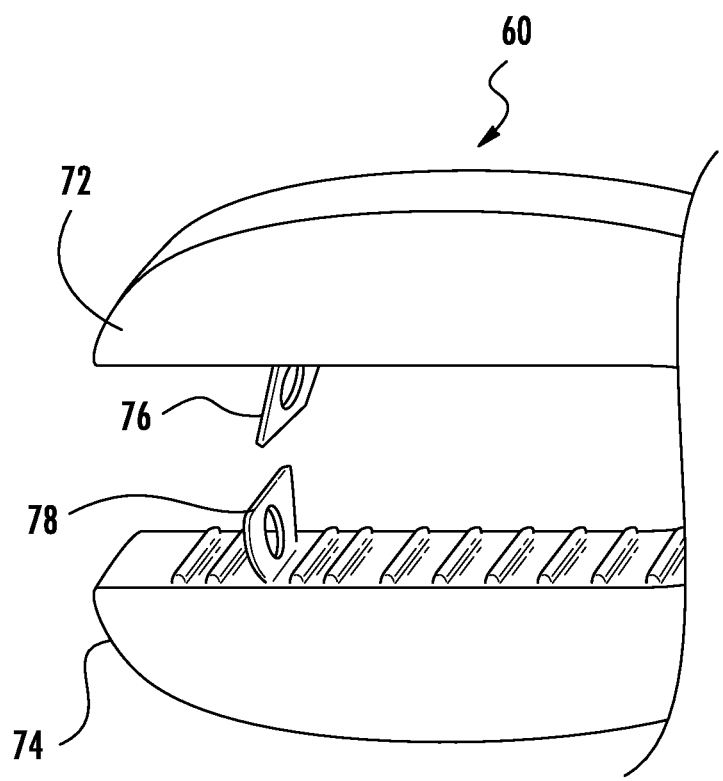
FIG. 17 is a partial perspective view of the tool assembly of the end effector of FIG. 1.

With particular reference now to FIGS. 16 and 17, each jaw member 72, 74 defines channel 90 configured and dimensioned to slidably receive cutting elements 76, 78 therein. Each cutting element 76, 78 is attached to respective flexible shaft 29a, 29b. Flexible shafts 29a, 29b extend through channel 90 defined in each jaw member 72, 74 and are connected to actuation rod 24 that is operatively coupled to actuation knob 20. Under such configuration, translation of articulation knob 20 (FIGS. 12 and 13) causes translation of cutting elements 76, 78 along respective channel 90, and thereby enabling movement of cutting elements 76, 78 in and out of respective channel 90. Additionally, rotation of actuation knob 20 causes rotation of end effector 60 about longitudinal axis "X-X" with respect to articulation neck assembly 40.

In addition, cutting elements 74, 76 may include either an active electrode or a return electrode such that when the electrodes are placed in close proximity to each other electrical circuit is formed between the two electrodes. When the electrodes are sufficiently separated from one another, the electrical circuit is open and thus inadvertent contact with body tissue with either of the separated electrodes does not cause current to flow. The cutting process is controlled by utilizing a switch 510 (FIG. 1) and a generator 500 (FIG. 1). Switch 510 is configured to selectively provide electrical energy to the electrodes to cut tissue disposed therebetween. For example, rocker switches, toggle switches, flip switches, dials, etc. are types of switches that can be commonly employed to accomplish this purpose. These switches can be placed anywhere on the instrument or may be configured as a remote switch, e.g., hand switch or a foot switch. Generator 500 delivers energy to tissue in a pulse-like waveform. RF pulsing may be used to more effectively cut tissue. For example, an initial pulse from the cutting element through the tissue (or the tissue contacting surfaces through the tissue) may be delivered to provide feedback to the smart sensor for selection of the ideal number of subsequent pulses and subsequent pulse intensity to effectively and consistently cut the amount or type of tissue.

The geometry of the electrodes may be configured such that the surface area ratios between the electrical poles focus electrical energy at tissue. An insulator is disposed adjacent channel 90. The insulator or insulative material may be of any suitable composition such as, for example, glass, polymeric, and ceramic materials. Moreover, the geometrical configurations of the electrodes and insulators may be designed such that they act like electrical sinks or insulators to influence the heat effect within and around tissue during the cutting processes.

With particular reference to FIG. 16, cutting elements 76, 78 may be substantially dull and are only capable of cutting tissue through application of electrical energy. However, it is also contemplated that cutting element 76, 78 may include blade portions that are capable of cutting tissue without the use of electrical energy.

Cutting elements 76, 78 may be disposed in general vertical registration to each other when actuation knob 20 is actuated (moved distally). Alternatively, a pair of cutting elements may be configured to be in general transverse registration when actuated. For example, each jaw may include a channel that is U-shaped, and the pair of cutting elements may be slidably disposed adjacent the respective lateral sides prior to actuation. Upon actuation, the cutting elements extend out of the jaw in general transverse registration. It is also contemplated that the cutting element may be rotatably mounted in a jaw member such that a cutting element disposed within the jaw member may be rotated to extend out of the jaw member when actuated. For example, the cutting elements may rotate about the ends of the jaw members, respectively. It is also envisioned that both the jaw members and the cutting elements may be curved, and the cutting elements may extend out along the curvature of the jaw members when actuated. During the cutting phase, highly concentrated electrical energy may travel from the cutting element through tissue to cut tissue. The number of pulses required to effectively cut tissue and the intensity of the cutting energy may be determined by measuring tissue impedance. A smart sensor (not shown) or feedback loop may be employed for this purpose.

It is also envisioned that a mechanical or electrical lockout mechanism that prevents cutting elements 76, 78 from being unintentionally activated when jaw members 72, 74 are disposed in the open configuration may be utilized. In addition, the nesting of cutting elements 76, 78 in respective channels 90 of respective jaw member 72, 74 further inhibits inadvertent contact. Moreover, utilization of both mechanical clamping action and electrical energy to cauterize and cut tissue specimen may result in less trauma to the patient and reduced healing time.

In use, the surgeon creates an incision through an intercostal space, such as the area between the ribs of a patient into a cavity, such as the thoracic cavity. It will be appreciated that the surgeon may enter any body cavity through any known procedure. A portal, known to those skilled in the art, may optionally be inserted into the incision to prevent the incision from closing. Reference may be made to U.S. Patent Application Publication Nos. 2012/0245427, filed on Feb. 10, 2012, and 2012/0283520, filed on Apr. 5, 2012, the entire contents of each of which are incorporated herein by reference, for a detailed discussion of the construction and operation of a portal. Surgical instrument 10 with jaw members 72, 74 in the closed, approximated configuration is inserted into the thoracic cavity (not shown). After surgical instrument 10 is positioned in the thoracic cavity, the surgeon may then adjust movable handle assembly 10 to orient jaw members 72, 74 toward the target site. Through articulation of neck assembly 40 and rotation of end effector 60, jaw members 72, 74 may be properly positioned adjacent the target site. As discussed hereinabove, approximation handle 16 may be squeezed to grasp tissue between jaw members 72, 74. Thereafter, actuation knob 20 may be moved distally to actuate cutting elements 76, 78 to achieve general vertical registration with each other. Reference may be made to U.S. Patent Application Publication No. 2008/0086154, filed on Oct. 6, 2006, the entire contents of which are incorporated herein by reference, for a detailed discussion of the construction and operation of an actuation mechanism.

Upon vertical registration of cutting elements 76, 78, the surgeon may activate switch 510 to effect cutting of the specimen, e.g., lymph node. Upon cutting of the specimen, cutting elements 76, 78 are retracted into the respective channel 90 in jaw member 72, 74, while the specimen is securely clamped between jaw members 72, 74. Once the specimen has been secured to jaw members 72, 74, surgical instrument 100 may be removed from the patient. Alternatively, the specimen may be transferred to a storage vessel prior to extraction from the patient. The surgical instrument 100 is then removed from the body of the patient and the specimen is removed from the cavity and placed in, for example, a proper receptacle for further examination. The obtained specimen, e.g., lymph node, may be delivered to a technician for further processing.

Although the illustrative embodiments of the present disclosure have been described herein with reference to the accompanying drawings, the above description, disclosure, and figures should not be construed as limiting, but merely as exemplifications of particular embodiments. Persons skilled in the art will understand that the devices and methods specifically described herein and illustrated in the accompanying drawings are non-limiting exemplary embodiments. For example, one skilled in the art may contemplate using a plurality of different cutting mechanisms of different shapes and sizes to cut, for example, a portion of tissue. Any combination of the above embodiments is also envisioned and is within the scope of the claimed invention. Moreover, the end effector 60 may comprise any suitable shape and material. Solely by way of example, the end effector 60 may comprise stainless steel or a biocompatible plastic. The end effector 60 may be substantially cylindrically-shaped. It is to be understood, therefore, that the disclosure is not limited to those precise embodiments, and that various other changes and modifications may be effected therein by one skilled in the art without departing from the scope or spirit of the disclosure.

The invention claimed is:

1. A surgical instrument, comprising:
a handle assembly including an actuation knob;
an elongate body extending distally from the handle assembly and defining a longitudinal axis;
a tool assembly operatively coupled to the handle assembly and extending from a distal end of the elongate body, the tool assembly including:
first and second jaw members each including an electrically conductive cutting element, the cutting elements operatively coupled to the actuation knob, the first and second jaw members defining respective channels configured to slidably receive the respective cutting elements, and respective apertures adjacent distal portions of the respective channels, wherein the cutting elements slide distally within the respective channels of the first and second jaw members and extend out of the respective apertures to be positioned in general vertical registration with each other to transfer electrical energy from the first jaw member to the second jaw member; and
an electrical energy source for providing electrical energy to at least one of the cutting elements.

2. The surgical instrument according to claim 1, wherein the first and second jaw members are movable between a spaced apart position and an approximated position in which the jaw members are adjacent to each other to clamp tissue therebetween.

3. The surgical instrument according to claim 2, further comprising an actuation rod interconnecting the actuation knob and the cutting elements, wherein translation of the actuation knob positions the cutting elements in vertical registration, and rotation of the actuation knob causes rotation of the first and second jaw members about the longitudinal axis.

4. The surgical instrument according to claim 3, further comprising an approximation rod extending through the elongate body and operatively coupled to the first and second jaw members, wherein translation of the approximation rod moves the first and second jaw members between the spaced apart and approximated positions.

5. The surgical instrument according to claim 4, wherein the approximation rod and the actuation rod are concentrically arranged.

6. The surgical instrument according to claim 5, wherein the handle assembly includes a slidable collar configured and adapted to slide over the elongate body, the slidable collar being operatively coupled with the approximation rod for a concomitant translation therewith.

7. The surgical instrument according to claim 1, further comprising an articulation assembly including a plurality of articulation links pivotably coupled to each other and at least a pair of articulation cables interconnecting the plurality of articulation links, wherein the at least a pair of articulation cables is operatively coupled to the handle assembly.

8. The surgical instrument according to claim 7, wherein the handle assembly further includes a rotatable hub defining a helical groove on an outer wall thereof, wherein proximal ends of the at least a pair of articulation cables are configured and adapted to slidably engage the helical groove, whereby rotation of the rotatable hub translates the at least a pair of articulation cables in opposite directions.

9. The surgical instrument according to claim 1, wherein the tool assembly is rotatable about the longitudinal axis.

10. The surgical instrument according to claim 1, wherein the cutting elements are substantially dull, the cutting elements being configured and adapted to cut tissue through application of electrical energy thereto.

11. The surgical instrument according to claim 1, wherein the first and second jaw members each include a tissue contacting surface having teeth configured and adapted to grasp tissue.

12. A method of removing tissue, the method comprising:
providing a surgical instrument including:
- an elongate body defining a longitudinal axis; and
- a tool assembly secured to a distal end of the elongate body, the tool assembly including first and second jaw members each including an electrically conductive cutting element slidably disposed therein, wherein the cutting elements slide distally within the respective channels and extend out of respective apertures adjacent distal portions of the respective channels to be positioned in general vertical registration to each other to transfer electrical energy through tissue positioned between the cutting elements to cut the tissue;

introducing the surgical instrument into a patient;
advancing the tool assembly toward a target tissue within the patient;
placing the target tissue between the first and second jaw members;
positioning the cutting elements in general vertical registration to each other;
cutting the target tissue positioned between the cutting elements; and
extracting the target tissue.

13. The method according to claim 12, wherein cutting the target tissue positioned between the cutting elements includes supplying electrical energy to the cutting elements.

14. The method according to claim 12, wherein advancing the tool assembly toward the target tissue includes articulating the tool assembly.

15. The method according to claim 12, wherein positioning the cutting elements in general vertical registration to each other includes translating an actuation knob operatively coupled to the cutting elements.

16. The method according to claim 12, further comprising translating an approximation rod extending through the elongate body and operatively coupled to the first and second jaw members to transition the first and second jaw members between the spaced apart and approximated positions.

17. The method according to claim 16, wherein translating the approximation rod includes sliding a slidable collar operatively coupled with the approximation rod for a concomitant translation therewith.

18. The method according to claim 12, wherein cutting the target tissue includes positioning the target tissue between substantially dull cutting elements and supplying electrical energy thereto.

19. The method according to claim 12, further comprising rotating the tool assembly about the longitudinal axis.

* * * * *